US011320335B2

(12) United States Patent
Ghasemvand et al.

(10) Patent No.: US 11,320,335 B2
(45) Date of Patent: May 3, 2022

(54) SYSTEMS AND METHODS FOR TESTING GAS LEAK DETECTORS

(71) Applicants: Mahmood Ghasemvand, Karaj (IR); Mohamad Samadi, Karaj (IR)

(72) Inventors: Mahmood Ghasemvand, Karaj (IR); Mohamad Samadi, Karaj (IR)

(*) Notice: Subject to any disclaimer, the term of this patent is extended or adjusted under 35 U.S.C. 154(b) by 385 days.

(21) Appl. No.: 16/676,367

(22) Filed: Nov. 6, 2019

(65) Prior Publication Data
US 2021/0131903 A1 May 6, 2021

(51) Int. Cl.
*G01M 3/20* (2006.01)
*G01M 3/22* (2006.01)
*G01N 33/00* (2006.01)
*G01F 25/10* (2022.01)

(52) U.S. Cl.
CPC .............. *G01M 3/207* (2013.01); *G01F 25/10* (2022.01); *G01M 3/223* (2013.01); *G01M 3/224* (2013.01); *G01N 33/0006* (2013.01); *G01N 33/007* (2013.01); *G01N 33/0016* (2013.01); *G01N 2033/0072* (2013.01)

(58) Field of Classification Search
CPC ...... G01M 3/207; G01M 3/223; G01M 3/224; G01F 25/10; G01N 33/0016; G01N 33/007; G01N 33/0072
See application file for complete search history.

(56) References Cited

U.S. PATENT DOCUMENTS

2013/0192332 A1* 8/2013 Scheffler .............. G01N 33/007
73/1.06
2018/0335409 A1* 11/2018 Kao .................... G01N 33/0047

FOREIGN PATENT DOCUMENTS

| CN | 2869839 Y | * | 2/2007 | |
| EP | 0302708 A2 | * | 2/1989 | .......... B01F 3/04836 |
| JP | 11183462 A | * | 7/1999 | |

* cited by examiner

*Primary Examiner* — David Z Huang

(57) ABSTRACT

A system and a method for accurately testing gas leak detectors by considering multiple operational parameters as per the standard requirements are disclosed. The system comprises one or more gas cylinders, a test execution chamber, mass flow controllers (MFCs), and a control system. The test execution chamber is connected to the gas cylinders via test gas pipelines and a plurality of valves, and the mass flow controllers. The test execution chamber further comprises a first chamber and a second chamber, which are connected to form a closed cycle, thereby saving consumption of the testing gases. The control system in communication with the mechanized system, thereby controlling the operation of the system for accurately testing the gas leak detector test samples. The performance of the one or more gas leak detector test samples is controlled by adjusting the density of the testing gas to a predetermined value and as per the standard requirements.

18 Claims, 3 Drawing Sheets

SYSTEMS AND METHODS FOR TESTING GAS LEAK DETECTORS

BACKGROUND OF THE INVENTION

Gas leak detectors or gas leakage alarming devices, for example, carbon monoxide and flammable gas leak detectors, are used for monitoring potentially hazardous gases in various environments. Generally, a sensor(s) within the gas leak detector is configured to detect hazardous gases within the environment by diffusion or by a forced flow of gases. Electronics within the gas leak detector convert the output signal from the sensor(s) into one or more signals representative of a gas concentration. The sensor output per unit amount of gas could vary with time and hence periodic calibration is required to ensure that the detector reading is accurate.

Similarly, leakage of urban gas may lead to the occurrence of explosive accidents with financial damages and fatalities among individual and families. Every year, inadvertent accidents take place throughout the world due to toxicity and asphyxiation with carbon monoxide.

As the vanguard devices for alarming of leakage of above-said gases, the gas leak detectors, for example, carbon monoxide and flammable gases leakage detectors may be utilized for alerting the individuals surrounding the environment and showing any suitable reaction to these accidents. The sensitivity of the performance of the gas leak detectors is directly related to life and properties of the individuals, so that the performance, quality of design, and production of the gas leak detectors is crucially important.

Unfortunately, it was not accurately possible to test and analyze the compliance of the gas leak detectors, for example, carbon monoxide and flammable gases leakage detectors with standard requirements because of the absence of advanced and technical equipment available. Thus, despite the compulsory implementation of standards for the gas leak detectors, the carbon monoxide and flammable gases leakage occur due to lack of possibility for conducting the related tests. The governing conditions in the consumption market have not changed and some low-quality and miscellaneous specimens of this device are still found in the market. In other words, lack of possible verification for quality of favorable devices and their calibration in the consumption market caused the manufacturer to fail in the market for competition with miscellaneous samples with low quality and the low cost was exclusively assumed as the criterion for valuation of an appropriate device in the consumption market.

Currently, sensors of gas detectors are calibrated by passing a calibration gas having known, fixed compositions of one or more analyte gases from a compressed gas cylinder into the detector, thereby displacing ambient air within the detector and exposing the sensor(s) to the calibration gas. The calibration gas is allowed to flow until the sensor output reaches a steady state. Many factors that are required for a standard test are not observed in this quality control process and at the initial test. Some different parameters including temperature, humidity, ambient pressure, the device voltage, velocity of testing gas, sound intensity, time period, and conditions for activation of alarm and circumstances for exiting from alarming status etc. are effective in conducting tests of European Standards No. EN 50291-1 and EN 50194-1 and their Equivalent American standards UL 2034 and UL 1484 each of which are controlled and surveyed online and constantly. It is not possible to manually control the gas leak detectors with respect to a multiplicity of these necessary parameters. Particularly in more complicated tests in which more processes should be measured at any moment, this uniform and constant control are not possible and occurrence of human errors and wrong calibrations are inevitable.

At present, existing standard tests are carried out manually discretely and with limited facilities. Given ambient parameters e.g. temperature, humidity, air pressure, velocity of testing gas, sound intensity, and operational voltage of device, uniform and continuous and perfect testing of standards of the gas leak detectors, for example, carbon monoxide and flammable gases leakage detectors are a very complex and vital process. Definition and structural formulation including hardware and suitable encoding for implementation of requirements of relevant standards are assumed as the paramount factor in this regard.

However, the conventional systems and methods require multiple components which increases the cost. At present, the above-said standard tests are carried out manually discretely and with the limited facilities. Given ambient parameters e.g. temperature, humidity, air pressure, velocity of testing gas, sound intensity and operational voltage of device, uniform and continuous and perfect testing of standards of the carbon monoxide and flammable gases leakage detectors is a very complex and vital process according to European standards No EN 50291-1 and EN 50194-1 and their equivalent American standards well-known as UL 2034 and UL 1484. Definition and structural formulation including hardware and suitable encoding for implementation of requirements of relevant standards are assumed as the paramount factor in this regard and the results are not accurate. Further, the conventional systems and methods are more complicated, with more processes to be measured at any moment, and the uniform and constant control of the system is not possible and occurrence of human errors and wrong calibrations are inevitable.

Therefore, there is a clear and present need for a system and a method for accurately testing one or more gas leak detectors by considering multiple operational parameters as per the standard requirements such as European standards No EN 50291-1 and EN 50194-1 and their equivalent American standards well-known as UL 2034 and UL 1484. Further, there is also a need to provide an inexpensive system and a method for accurately testing one or more gas leak detectors using a control system to obtain effective test results of the one or more gas leak detectors.

SUMMARY OF THE INVENTION

The present invention generally relates to a system and method for executing tests in order to verify products as per standard requirements and more particularly relates to a system and method for accurately executing tests in order to effectively verify the gas leak detectors as per standard requirements.

In one embodiment, the mechanized system is configured to accurately execute tests on the one or more gas leak detector test samples as per standard requirements according to European standards No EN 50291-1 and EN 50194-1 and their equivalent American standards No UL 2034 and UL 1484 by considering multiple operational parameters. In one embodiment, the mechanized system comprises one or more gas cylinders, a test execution chamber, and one or more mass flow controllers (MFCs) and different measuring instruments and data logger. The gas cylinders are configured to store testing gases with different concentrations. In one embodiment, the gas cylinders are could be, but not limited to, a zero air gas cylinder, a pure and diluted gases cylinder ($CO/CH_4$), a mixed gases cylinder ($H_2$, $CO$, $CO_2$), a zero gas cylinder, a hexamethyldisiloxane gas cylinder, a ethanol gas cylinder, a toluene gas cylinder, a acetone gas cylinder, a nitric oxide (NO) gas cylinder, and a sulfur dioxide ($SO_2$) gas cylinder respectively.

In one embodiment, the test execution chamber/temperature isolation chamber is connected to the gas cylinders via test gas pipelines and a plurality of valves. In one embodiment, one or more gas purge systems are securely affixed to the one or more gas cylinders such as the pure gases cylinder ($CO/CH_4$), the nitric oxide (NO) gas cylinder, and the sulfur dioxide ($SO_2$) gas cylinder. The gas purge systems are used to discharge unclean and impure and intrusive gases from gas transfer pipelines and tubes. In one embodiment, the mass flow controllers are securely positioned between the gas cylinders and the test execution chamber.

The mass flow controllers are configured to measure and control the flow of the testing gases. In one embodiment, the testing gases are at least any one or any combination of, but not limited to, a zero air gas, pure and diluted gases ($CO/CH_4$), mixed gases ($H_2$, $CO$, $CO_2$), a hexamethyldisiloxane gas, a ethanol gas, a toluene gas, a acetone gas, a nitric oxide (NO) gas, and a sulfur dioxide ($SO_2$) gas. In one embodiment, a humidifier is connected to the test execution chamber via the test gas pipeline and the valves. The humidifier is configured to maintain and increase the humidity (moisture) within the test execution chamber. In one embodiment, an inlet valve is provided to the test execution chamber for allowing environment air within the test execution chamber. In one embodiment, the plurality of valves and the inlet valve could be, but not limited to, solenoid valves.

In one embodiment, the test execution chamber comprises at least two chambers such as a first chamber and a second chamber wherein the gas leak detector test samples inside them for performance related standards tests. In one embodiment, the first chamber and the second chamber of the test execution chamber are connected to form a closed cycle via the test gas pipeline, a circulation pump, and a solenoid valve, thereby providing the potential for saving in consumption of the testing gases. If a chamber is utilized for this purpose, the gas should be used with controlled flow and velocity to create velocity for testing gas as standard requirements and this gas should enter permanently from a path into the chamber and exit from another path. This problem might increase consumption of testing gas and lead to wasting gas and with respect to high price of testing and laboratory gases, this might increase cost for conducting tests. In one embodiment, an anemometer is securely connected between the second chamber and the circulation pump via the test gas pipeline. In one embodiment, the anemometer could be, but not limited to, a digital air anemometer.

The velocity of the testing gases could be controlled using the anemometer and a dimmer. In one embodiment, the test execution chamber comprises a heating system/heater and a cooling system/freezer. The heating system and the cooling system are configured to adjust the temperature within the test execution chamber, thereby maintaining stability in the test execution chamber (first chamber and a second chamber) for controlling under conditions of ambient or special temperature. In one embodiment, the test execution chamber further comprises an outlet for allowing the testing gases to outside via the solenoid valve using a vacuum pump.

In one embodiment, the first chamber of the test execution chamber comprises, but not limited to, a temperature sensor/transmitter, a humidity sensor/transmitter, and a sound level meter. In one embodiment, the second chamber of the test execution chamber comprises, but not limited to, a data logger and an input for power supply for the test samples. The data logger is configured to record data related to, but not limited to, temperature, humidity, power supply voltage and ambient pressure, etc. from one or more sensors and transmitters. In one embodiment, the test execution chamber further comprises one or more sensors and transmitters and devices for monitoring and controlling the test execution chamber. In one embodiment, the one or more sensors and transmitters and devices are at least any one or any combination of, but not limited to, a temperature sensor, a humidity sensor, an air pressure sensor, an audiometer and a digital air anemometer.

In one embodiment, the mechanized system further comprises an uninterrupted power supply (UPS) for supplying power to the mechanized system using an autotransformer (Variac), thereby controlling the operational voltage of the gas leak detectors. In one embodiment, a voltmeter or a volt transmitter is operatively connected to across the autotransformer for measuring the voltage of the power supply. In one embodiment, the gas leak detectors are securely connected to the second chamber of the test execution chamber via the plurality of valves and the sampling pumps through the testing gases pipeline.

In one embodiment, the mechanized system further comprises a control system and a monitoring system. The control system in communication with the mechanized system and the monitoring system, thereby controlling the operation of the mechanized system for accurately testing the gas leak detector test samples by considering the multiple operational parameters. In one embodiment, the operational parameters include, but not limited to, temperature, humidity, test gas velocity, air pressure, sound intensity, operational voltage of the system, performance status of the cooling system, the heating system, the humidifier, the dryer, the sampling pump, the vacuum pump, the circulation pump, density of the testing gases with activation of a special industrial gas detectors or Analyzers of the same testing gas, the status of the plurality of valves of the gas cylinders, the performance status of the one or more gas leak detectors, and the potential for selection and injection of suitable testing gases for executing the test according to European standards No EN 50291-1 and EN 50194-1 and their equivalent American standards No UL 2034 and UL 1484.

In one embodiment, the control system comprises a programmable logic controller (PLC), configured to control the operation of the mechanized system. In one embodiment, the control system is in communication with, but not limited to, the plurality of valves, the mass flow controllers, the humidifier, the uninterrupted power supply, the autotransformer, the test execution chamber, the industrial gas detectors or analyzers, the sampling pumps, and the vacuum pump via data transfer lines.

In one embodiment, two methods for accurately testing one or more gas leak detector test samples using the mechanized system by considering multiple operational parameters as per standard requirements is disclosed. In one embodiment, the methods comprise two ways. At one way, the existing air of test execute chamber comprises of first chamber and second chamber draining via vacuum pump, afterward the one or more testing gases with different and defined concentrations are transferring and controlled injecting from one or more gas cylinders into a test execution chamber and first chamber via the test gas pipelines, the plurality of valves, and the mass flow controllers (MFCs). In this way and for adjusting the density of the testing gas to a predetermined value as per standard requirements, due to first and second chambers volume capacity and testing gas defined concentration and gases flow ratio of mass flow controllers (MFCs), control system calculate the injecting time of defined testing gas. Therefor the injected testing gases uniformly circulating in test execution chamber from first chamber to second chamber and the mechanized system controlling performance of gas leak detector test samples as per standard requirements.

At another way, the one or more testing gases with different concentrations are transferring and controlled injecting from one or more gas cylinders into a test execution chamber and first chamber via the test gas pipelines, the plurality of valves, and the mass flow controllers (MFCs). Afterward, the testing gases uniformly circulating in test execution chamber from first chamber to second chamber. Then, the sampling process is performed by obtaining samples of the testing gas within the test executing chamber via sampling and analyzed the sampled testing gas with industrial gas detectors or analyzers. With the result of sampled testing gas analyzing, control system make decisions for change and increase or decrease the made testing gas concentration via pure or diluted testing gases or zero air gas, or accept the made testing gas concentration as per standard requirements and controlling performance of the one or more gas leak detector test samples. Further, the testing results of the one or more gas leak detector test samples are declared, thereby verifying and testing the performance of the one or more gas leak detector test samples as per the standard requirements.

In one embodiment, three events may be anticipated by analysis on the made testing gas: a) Concentration made by testing gas is equal to the standard requirements; b) The made concentration by testing gas is greater than standard requirements; and c) The given concentration in testing gas is smaller than standard requirements. Mechanized system enters the next step for execution of test in mode (a) according to the related standard. In mode (b), mechanized system discharges some part of testing gas inside the given chamber by activation of vacuum pump and adjustable timetable and then injects some zero air into chamber for conducting text by adjustable timetable and afterwards mechanized system makes new concentration homogeneous and uniform. Again, sampling pumps take sample of made testing gas and then testing gas is analyzed by industrial gas detector or analyzers and this cycle is continued until the favorable result is obtained with the given specific concentration and density. Under mode (c), if the result of testing gas analysis shows that the compression of produced testing gas differs from concentration of the given testing gas more than 20% (this scale is also adjustable at this level) mechanized system uses again pure gas with high density for ease of use, precision and time-saving and it is injected into the chamber and it takes sample and analyzes sample after homogenization and making sample uniform. However, if the result of analysis on testing gas indicates that difference is lesser than 20% (this scale is also adjustable at this level) between concentration level in the made testing gas with density of the given testing gas, mechanized system uses diluted gas capsule with low density and injects the diluted gas into testing chamber by adjustable timetable and after being homogeneous and uniform in first and second test chambers, it takes sample and analyzes the newly made testing gas and again it is decided for repetition of one of (a), (b) and (c) processes. This inventive technique may highly contribute to quick and precise make of testing gas at this phase.

One aspect of the present disclosure is directed to a testing mechanized system for testing one or more gas leak detector by considering multiple operational parameters as per standard requirements, comprising: (a) one or more gas cylinders with purge systems configured to store testing gases with different concentrations; (b) a test execution chamber connected to the one or more gas cylinders via test gas pipelines and a plurality of valves, wherein the test execution chamber comprises a first chamber, a second chamber, measuring instruments and data logger, (c) one or more mass flow controllers (MFCs) securely positioned between the one or more gas cylinders and the test execution chamber, wherein the mass flow controllers are configured to measure and control the flow of the testing gases, and (d) one or more industrial gas detectors or analyzers securely connected to the second chamber of the test execution chamber via the test gas pipelines, sampling pumps, and a plurality of valves, thereby transferring the testing gases to the one or more gas leak detectors or analyzers for verifying and testing the performance of the one or more gas leak detectors as per standard requirements.

In one embodiment, the system further comprises an uninterrupted power supply (UPS) for supplying power to the testing mechanized system and using an autotransformer and a digital voltmeter or volt transmitter, thereby controlling operational voltage of the one or more gas leak detector test samples. In one embodiment, a humidifier is used to configure to maintain and increase the humidity (moisture) within the test execution chamber and using a dryer is configured to maintain and decrease the humidity (moisture) within the test execution chamber.

In another embodiment, the system further comprises a control system, wherein the control system in communication with a monitoring system and the testing mechanized system, thereby enhancing control the operation of the testing mechanized system for testing one or more gas leak detector test samples by considering operational parameters, wherein the one or more gas leak detector test samples are carbon monoxide and flammable gases leakage detectors.

In one embodiment, the control system includes a programmable logic controller (PLC) and/or a microprocessor and/or a microcontroller for controlling the operation of the testing mechanized system. In another embodiment, the first chamber and the second chamber of the test execution chamber are connected to form a closed cycle, thereby providing the potential for saving in consumption of the testing gases, wherein velocity of testing gases between first chamber and second chamber is made with a circulation pump and controlled via a dimmer. In one embodiment, the testing gases are at least any one or any combination of a zero air gas, pure gases ($CO/CH_4$), diluted gases ($CO/CH_4$), mixed gases ($H_2$, $CO$, $CO_2$), a hexamethyldisiloxane gas, a ethanol gas, a toluene gas, a acetone gas, a nitric oxide (NO) gas, a sulfur dioxide ($SO_2$) gas. In another embodiment, the test execution chamber further comprises one or more sensors and transmitters and devices for monitoring and controlling the test execution chamber, wherein the one or more sensors and transmitters and devices are at least any one or any combination of a temperature sensor, a humidity sensor, an air pressure sensor, an audiometer, a digital air anemometer and a data logger. The logger is used for registering the temperature, humidity, ambient air pressure and electrical power voltage parameters.

In one embodiment, the test execution chamber further comprises a heating system and a cooling system, wherein the heating system and the cooling system are configured to adjust the temperature, thereby maintaining stability in the test execution chamber for controlling under conditions of ambient or special temperature. In another embodiment, the multiple operational parameters include temperature, humidity, air pressure, test gas velocity, sound intensity, operational voltage of the testing mechanized system, the performance status of the cooling system, the heating system, a humidifier, the dryer, the sampling pumps, the vacuum pump, the circulation pump, the density of the testing gases with activation of a special industrial gas detectors or analyzers of the same testing gas, the status of the plurality of valves, test results, hour and date of the test execution, operator related parameters, the performance status of the one or more gas leak detector test samples in terms of alarm and timetable for exiting from alarming status, indication and recording described timetables in standard requirements for activation of audiovisual alarms and exiting from alarming status, and potential for selection and injection of suitable testing gases for an operational test. In one embodiment, the plurality of valves are solenoid valves. In one embodiment, the plurality of valves are solenoid valves.

Another aspect of the present disclosure is directed to a method for testing one or more gas leak detector test samples using a testing mechanized system by considering multiple operational parameters as per standard requirements, comprising the steps of: (a) vacuuming existing air from test execute chamber, calculating injecting time due to first and second chambers' volume capacity, testing the gas defined concentration, and the gases flow ratio of mass flow controllers (MFCs), and then transferring, controlled injecting and uniformly circulating one or more testing gases with different and defined concentrations from one or more gas cylinders into a test execution chamber via test gas pipelines, a plurality of valves, and one or more mass flow controllers (MFCs); (b) in second way, transferring, controlled injecting and uniformly circulating different concentration of test gases via test gas pipelines, a plurality of valves, and one or more mass flow controllers (MFCs), and performing a sampling process by obtaining a part of the testing gas within the test execution chamber and analyzing the sampled testing gas with industrial gas detectors or analyzers; (c) controlling the performance of the one or more gas leak detector test samples as per standard requirements by adjusting the density of the referenced or sampled testing gas to a predetermined value and as per the standard requirements; (d) making decision for compliance or non-compliance of the one or more gas leak detectors test samples with the standard requirements, and (e) declaring testing results of the one or more gas leak detector test samples and, thereby verifying and testing the performance of the one or more gas leak detectors as per the standard requirements.

In one embodiment, the testing mechanized system comprises an uninterrupted power supply (UPS) for supplying power to the testing mechanized system and using an autotransformer and a digital voltmeter or volt transmitter, thereby controlling the operational voltage of the one or more gas leak detectors. In another embodiment, the testing mechanized system further comprises a control system, wherein the control system in communication with a monitoring system and the testing mechanized system, thereby controlling the operation of the testing mechanized system for testing the one or more gas leak detectors by considering multiple operational parameters and different concentration of pure or/and diluted or/and mixed testing gases. In one embodiment, the control system includes a programmable logic controller (PLC) and/or a microprocessor and/or a microcontroller for controlling the operation of the testing mechanized system.

In another embodiment, the test execution chamber comprises a first chamber and a second chamber, wherein the first chamber and the second chamber of the test execution chamber are connected to form a closed cycle, thereby providing the potential for saving in consumption of the testing gases. In one embodiment, the testing gases are at least any one or any combination of, but not limited to, a zero air gas, pure gases ($CO/CH_4$), diluted gases ($CO/CH_4$), mixed gases ($H_2$, $CO$, $CO_2$), a hexamethyldisiloxane gas, a ethanol gas, a toluene gas, a acetone gas, a nitric oxide (NO) gas, and a sulfur dioxide ($SO_2$) gas. In another embodiment, the test execution chamber further comprises one or more sensors and transmitters and devices for monitoring and controlling the test execution chamber, wherein the one or more sensors and devices are at least any one or any combination of a temperature sensor, a humidity sensor, an air pressure sensor, an audiometer, a digital air anemometer and a data logger.

In one embodiment, the test execution chamber further comprises a heating system and a cooling system, wherein the heating system and the cooling system are configured to adjust the temperature, thereby maintaining stability in the test execution chamber for controlling under conditions of ambient temperature. In another embodiment, the multiple operational parameters include temperature, humidity, air pressure, sound intensity, operational voltage of the system, performance status of the cooling system, the heating system, a humidifier, density of the testing gases with activation of a special industrial gas detectors or analyzers of the same testing gas, the status of the plurality of valves, the performance status of the one or more gas leak detectors, and potential for selection and injection of suitable testing gases for an operational test. In one embodiment, the density and concentration of the made testing gas is adjusted as per the standard requirements by controlling the injections of the diluted and mixed testing gases ($H_2$, $CO$, $CO_2$), the hexamethyldisiloxane gas, the ethanol gas, the toluene gas, the acetone gas, the zero air gas, the pure gases ($CO/CH_4$), diluted gases ($CO/CH_4$), the nitric oxide (NO) gas and the sulfur dioxide ($SO_2$) gas within the test execution chamber.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The present invention generally relates to a system and method for executing tests in order to verify products as per standard requirements and more particularly relates to a system and method for accurately executing tests in order to effectively verify the gas leak detectors as per standard requirements.

A description of embodiments of the present invention will now be given with reference to the figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
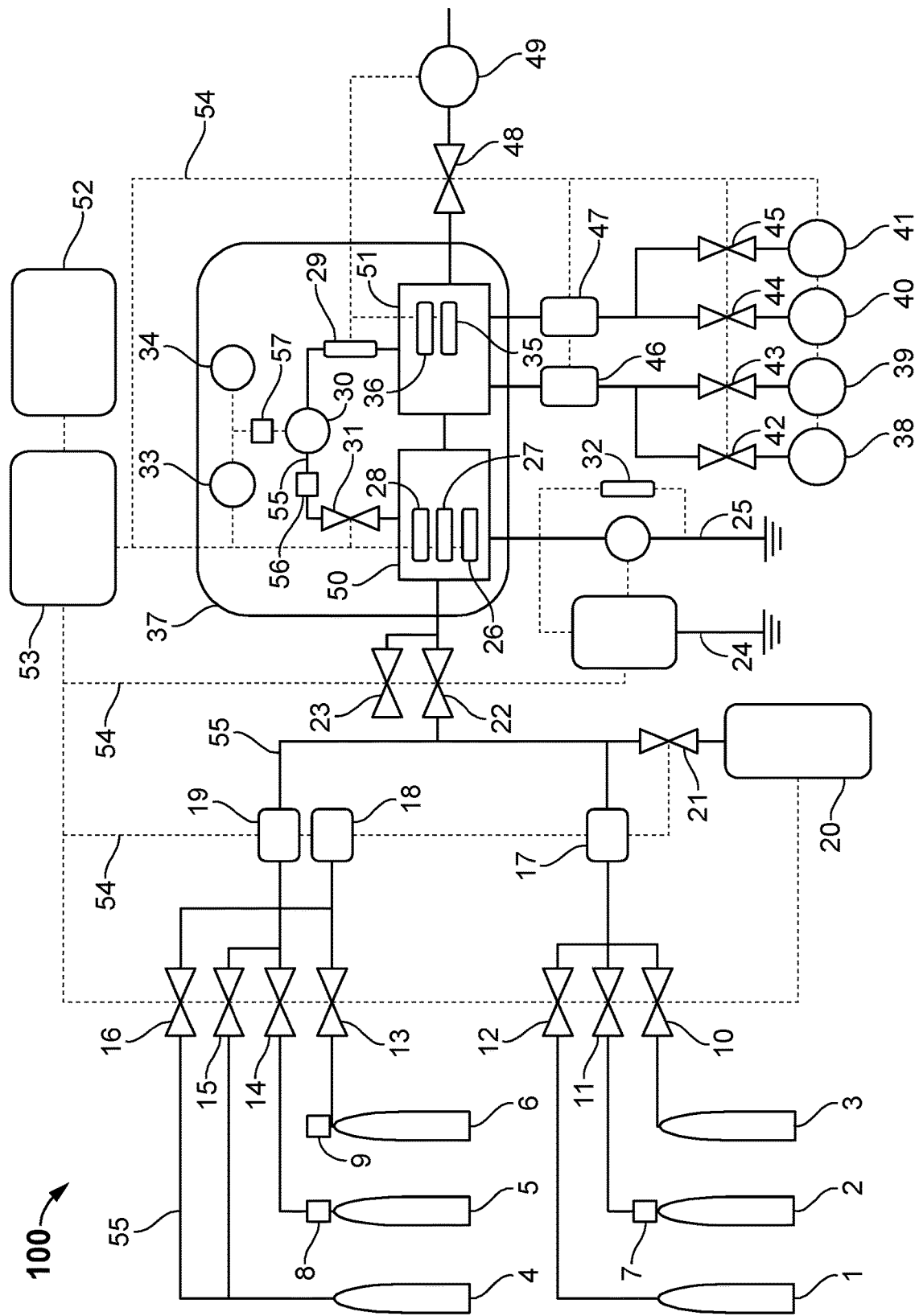
FIG. 1 illustrates a block diagram of a testing mechanized system for testing one or more gas leak detectors as per standard requirements according to an embodiment of the present invention.

Referring to FIG. 1, a testing mechanized system 100 for testing one or more gas leak detector test samples as per standard requirements is disclosed. In one embodiment, the system 100 is configured to accurately execute tests on the one or more gas leak detector test samples (which are installed inside the second chamber 51) as per standard requirements according to European standards No EN 50291-1 and EN 50194-1 and their equivalent American standards No UL 2034 and UL 1484 by considering multiple operational parameters. In one embodiment, the system 100 comprises one or more gas interchangeable cylinders (1, 2, 3, 4, 5, and 6), a test execution chamber 37, and one or more mass flow controllers (MFCs) (17, 18, and 19). The gas cylinders (1, 2, 3, 4, 5, and 6) are configured to store testing gases with different concentrations. In one embodiment, the gas cylinders (1, 2, 3, 4, 5, and 6) are could be, but not limited to, zero air gas cylinder, pure gases cylinder (CO/$CH_4$), diluted gases cylinder (CO/$CH_4$), a mixed gases cylinder ($H_2$, CO, $CO_2$), a hexamethyldisiloxane gas, a ethanol gas, a toluene gas, a acetone gas, a nitric oxide (NO) gas cylinder, and a sulfur dioxide ($SO_2$) gas cylinder, respectively.

In one embodiment, the test execution chamber/temperature isolation chamber 37 is connected to the gas cylinders (1, 2, 3, 4, 5, and 6) via test gas pipelines 55 and a plurality of valves (10, 11, 12, 13, 14, 15, and 16). In one embodiment, one or more gas purge systems (7, 8, and 9) are securely affixed to the one or more gas cylinders (2, 5, and 6) for pure or toxic or corrosive gases such as the carbon monoxide/methan gases (CO/$CH_4$) cylinder, the nitric oxide (NO) gas cylinder, and the sulfur dioxide ($SO_2$) gas cylinder.

The gas purge systems (7, 8, and 9) are used to discharge unclean and impure and intrusive gases from gas transfer pipelines and tubes. In one embodiment, the mass flow controllers (17, 18, and 19) are securely positioned between the gas cylinders (1, 2, 3, 4, 5, and 6) and the test execution chamber 37. The mass flow controllers (17, 18, and 19) are configured to measure and control the flow of the testing gases. In one embodiment, the testing gases are at least any one or any combination of, but not limited to, a zero air gas, pure gases (CO/$CH_4$), diluted gases cylinder (CO/$CH_4$), mixed gases ($H_2$, CO, $CO_2$), a hexamethyldisiloxane gas, a ethanol gas, a toluene gas, a acetone gas, a nitric oxide (NO) gas, and a sulfur dioxide ($SO_2$) gas. In one embodiment, a humidifier 20 is connected to the test execution chamber 37 via the test gas pipeline 55 and the valves (21 and 22).

The humidifier 20 is configured to maintain and increase the humidity (moisture) within first chamber 50 and a second chamber 51. The dryer 56 is configured to maintain and decrease the humidity (moisture) within first chamber 50 and a second chamber 51. In one embodiment, an inlet valve 23 is provided to first chamber 50 for allowing environment air within the first chamber 50 and a second chamber 51. In one embodiment, the plurality of valves (10, 11, 12, 13, 14, 15, 16, 21, and 22) and the inlet valve 23 could be, but not limited to, solenoid valves.

In one embodiment, the test execution chamber 37 comprises at least two chambers such as a first chamber 50 and a second chamber 51 which gas leak detector test samples are installed inside the second chamber 51 for performance related standards tests. In one embodiment, the first chamber 50 and the second chamber 51 of the test execution chamber 37 are connected to form a closed cycle via the test gas pipeline 55, a circulation pump 30, and a solenoid valve 31, thereby providing the potential for saving in consumption of the testing gases. In one embodiment, an anemometer 29 is securely connected between the second chamber 51 and the circulation pump 30 via the test gas pipeline 55. In one embodiment, the anemometer 29 could be, but not limited to, a digital air anemometer.

The velocity of the testing gases could be controlled using the anemometer 29 and a dimmer 57. In one embodiment, the test execution chamber 37 comprises a heating system/heater 33 and a cooling system/freezer 34. The heating system 33 and the cooling system 34 are configured to adjust the temperature within the test execution chamber 37 and especially within the first chamber 50 and a second chamber 51, thereby maintaining stability in the test execution chamber 37 for controlling under conditions of ambient and special temperature. In one embodiment, the test execution chamber 37 further comprises an outlet for allowing test gases to outside via the solenoid valve 48 using a vacuum pump 49.

In one embodiment, the first chamber 50 of the test execution chamber 37 comprises, but not limited to, a temperature sensor/transmitter 26, a humidity sensor/transmitter 27, and a sound level meter 28. In one embodiment, the second chamber 51 of the test execution chamber 37 comprises, but not limited to, a data logger 35 and an input 36 for power supply for the test samples. The gas leak detector test samples are installed inside the second chamber 51 too. The data logger 35 is configured to record data related to, but not limited to, temperature, humidity, ambient pressure and power supply voltage, etc. from one or more sensors and transmitters. In one embodiment, the test execution chamber 37 further comprises one or more sensors and transmitters and devices for monitoring and controlling the first chamber 50 and a second chamber 51. In one embodiment, the one or more sensors and transmitters and devices are at least any one or any combination of, but not limited to, a temperature sensor, a humidity sensor, an air pressure sensor, an audiometer, and a digital air anemometer.

In one embodiment, the system 100 further comprises an uninterrupted power supply (UPS) 24 for supplying power to the testing mechanized system 100 using an autotransformer (Variac) 25, thereby controlling the operational voltage of the gas leak detector test samples. In one embodiment, a voltmeter 32 is operatively connected to across the autotransformer 25 for measuring the voltage of the power supply. In one embodiment, the industrials gas detectors or analyzers (38, 39, 40, and 41) are securely connected to the second chamber 51 of the test execution chamber 37 via the plurality of valves (42, 43, 44, and 45) and the sampling pumps (46 and 47) through the test gas pipeline 55.

In one embodiment, the system 100 further comprises a control system 52 and a monitoring system 53. The control system 52 in communication with the system 100 and the monitoring system 53, thereby controlling the operation of the system 100 for accurately testing the gas leak detector test samples by considering the multiple operational parameters. In one embodiment, the operational parameters include, but not limited to, temperature, humidity, air pressure, test gas velocity, sound intensity, operational voltage of the gas leak detector test samples, performance status of the cooling system 34, the heating system 33, the humidifier 20, the dryer 56, the sampling pumps 46, 47, the vacuum pump 49, the circulation pump 30, density of the testing gases with activation of a special industrial gas detectors or analyzers (38, 39, 40, and 41) of the same testing gas, the status of the plurality of valves (10, 11, 12, 13, 14, 15, and 16) of the gas cylinders (1, 2, 3, 4, 5, and 6), hour and date of the test execution, operator related parameters, tests result, the performance status of the one or more gas leak detector test samples in terms of aural alarm and timetable for exiting from alarming status, indication and recording described timetables in standard requirements for activation of audio-visual alarms and exiting from alarming status, and the potential for selection and injection of suitable testing gases for executing the test according to European standards No EN 50291-1 and EN 50194-1 and their equivalent American standards No UL 2034 and UL 1484.

In one embodiment, the control system 52 comprises a programmable logic controller (PLC), configured to control the operation of the system 100. In one embodiment, the control system 52 is in communication with, but not limited to, the plurality of valves (10-16, 21-23, 31, 42-45, and 48), the heater 33, the freezer 34, the mass flow controllers (17, 18, and 19), the humidifier 20, the dryer 56, the dimmer 57, the uninterrupted power supply 24, the autotransformer 25, the test execution chamber 37, the temperature sensor/transmitter 26, humidity sensor/transmitter 27, the audiometer 28, the air anemometer 29, data logger 35, the industrial gas detectors or analyzers (38, 39, 40, and 41), the sampling pumps (46 and 47), the circulation pump, and the vacuum pump 49 via data transfer lines 54. In one embodiment, the industrial gas detectors or analyzers (38, 39, 40, and 41) are positioned outside of the test execution chamber 37, thereby preventing the industrial gas detectors or analyzers (38, 39, 40, and 41) from constant, erosive and long-term contact with the testing gases and thus reduced their precision and useful life.

Figure 2A:
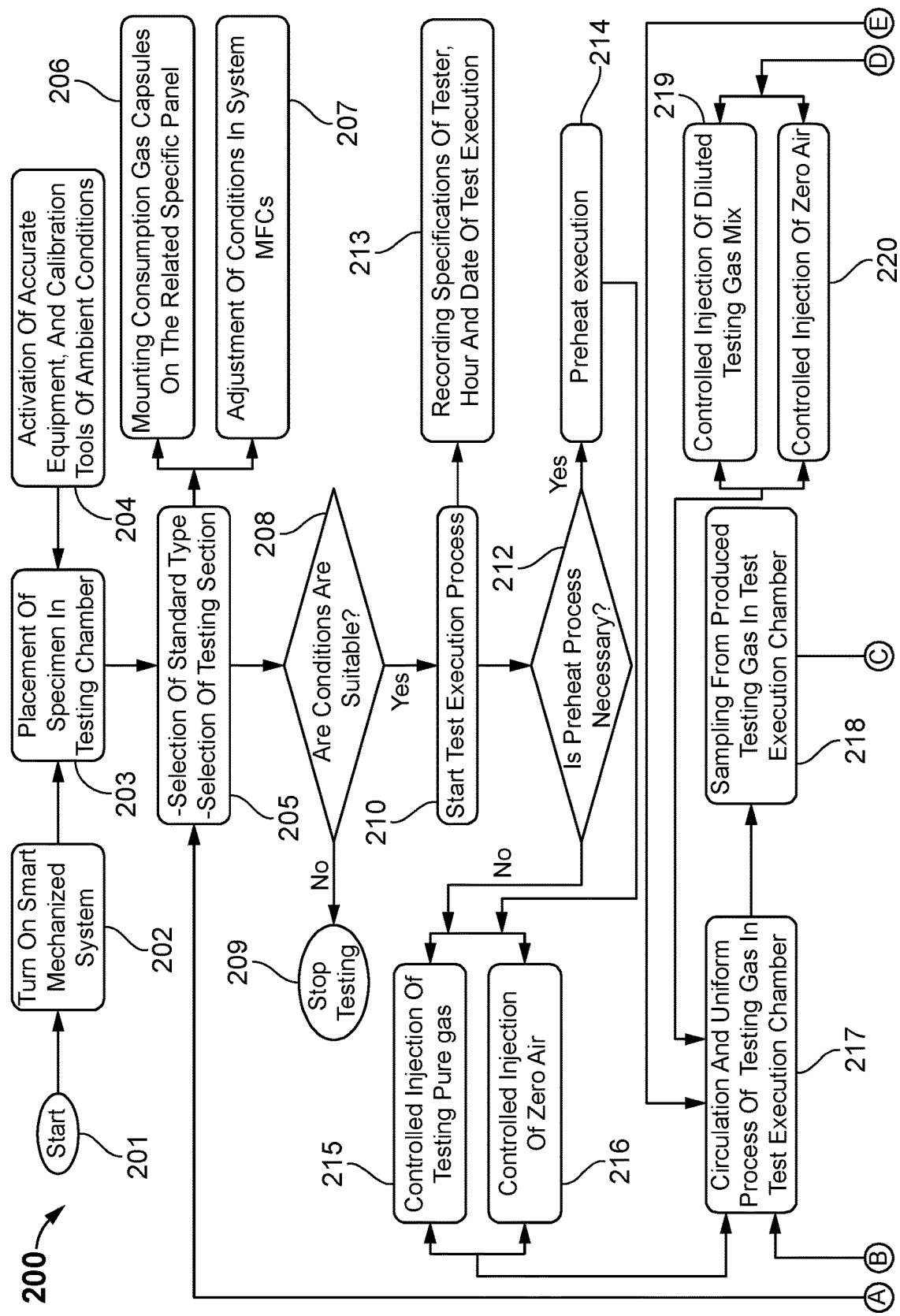
FIGS. 2A-2B illustrates a flowchart of a process for testing one or more gas leak detectors as per standard requirements using the testing mechanized system according to one embodiment of the present invention.
Figure 2B:
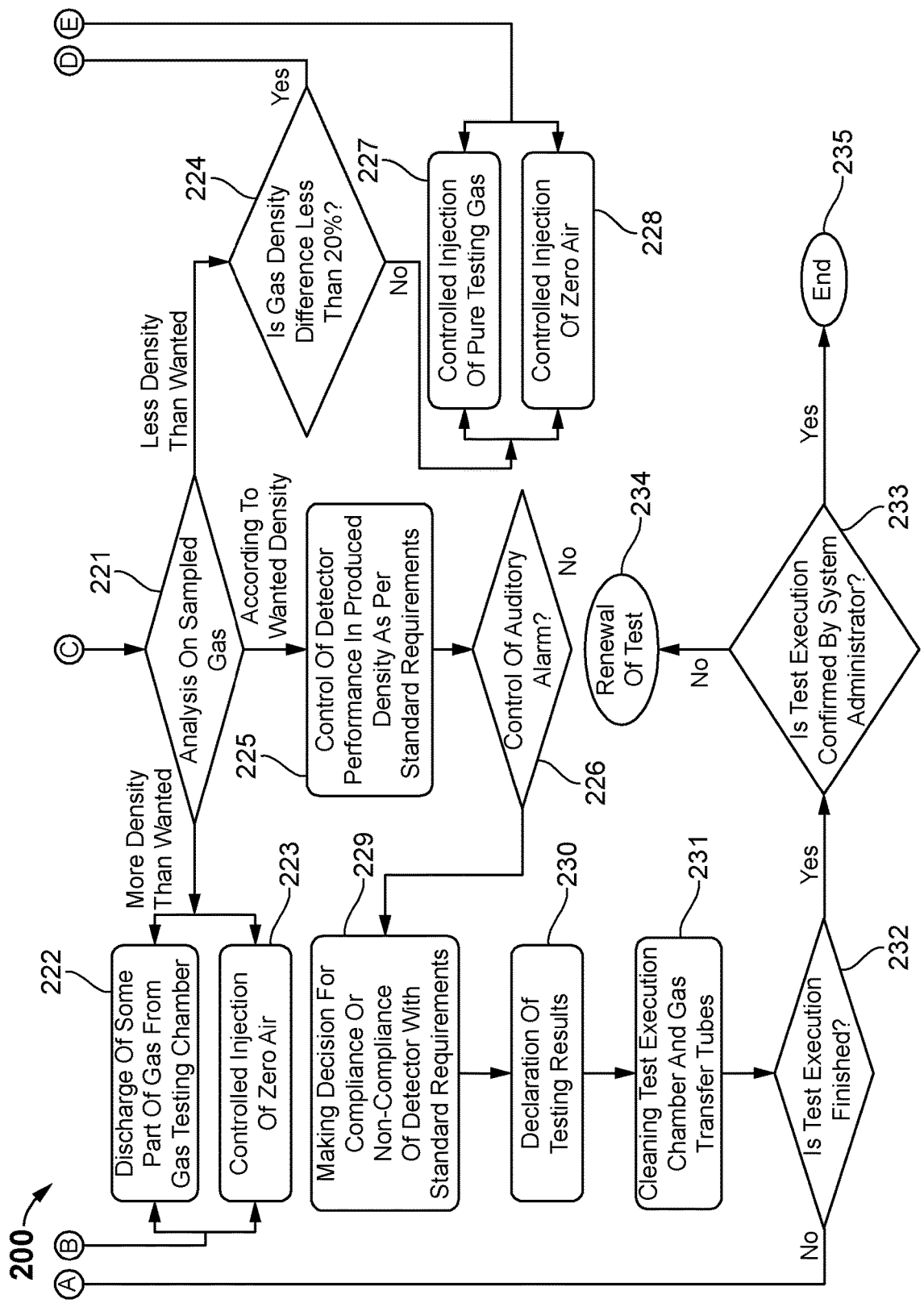

Referring to FIGS. 2A-2B, the flowchart of a method 200 for testing the one or more gas leak detector test samples as per standard requirements is disclosed. In one embodiment, the method 200 could be used for testing the as leak detector test samples as per standard requirements according to European standards No EN 50291-1 and EN 50194-1 and their equivalent American standards No UL 2034 and UL 1484 by considering multiple operational parameters. In one embodiment, the method 200 comprises a plurality of steps. At step 201, the method 200 is started and the system 100 is turned on at step 202. At step 203, a specimen (gas leak detector test samples) could be placed within the test execution chamber 37 and within second chamber 51 of the system 100.

At step 204, the user could activate the equipment of the system 100 and calibration tools of ambient conditions. In one embodiment, the equipment and calibration tools include, but not limited to, the temperature sensor/transmitter 26, humidity sensor/transmitter 27, the audiometer 28, the air anemometer 29, data logger 35, the plurality of valves (10-16, 21-23, 31, 42-45, and 48), the mass flow controllers (17, 18, and 19), the humidifier 20, dryer 56, the uninterrupted power supply 24, the autotransformer 25, the test execution chamber 37, the industrial gas detectors or analyzers (38, 39, 40, and 41), the sampling pumps (46 and 47), the circulation pump 30, and the vacuum pump 49. At step 205, the user could select the standard type such as, but not limited to, European standards No EN 50291-1 and EN 50194-1 and their equivalent American standards No UL 2034 and UL 1484 and testing section. At step 206, one or more interchangeable gas cylinders (1, 2, 3, 4, 5, and 6) are mounted on the related specific panel. At step 207, the operator/user could adjust conditions within the system 100 using the mass flow controllers (17, 18, and 19). The mass flow controllers (17, 18, and 19) are configured to measure and control the flow of the testing gases.

At step 208, the user/operator could check the conditions of the system 100 for executing the selected tests. At step 209, if the conditions of the system 100 are not suitable for the selected tests then the test execution process is terminated or stopped. At step 210, if the conditions of the system 100 are suitable for the selected tests then the test execution process is started. At step 213, the specifications of the tester and the corresponding date and time of the test execution is recorded. At step 212, the system 100 will check whether the preheat process is required or not. At steps 215-216, if the system 100 does not require the preheat process then the injection of testing pure gases ($CO/CH_4$) and the zero air gas are controlled. At step 214, if the system 100 requires the preheat process then the preheat process is executed by controlling the injection of testing pure gases ($CO/CH_4$) and the zero air gas. At step 217, the testing gases are uniformly transferred and circulated within the test execution chamber 37 between first chamber 50 and second chamber 51.

At steps 219-220, the injection of diluted and mixed testing gases and the zero air gas are controlled. At step 218, the sampling process is performed by obtaining samples of the testing gas within the test executing chamber 37 in first chamber 50 and second chamber 51. At step 221, the sampled testing gas is analyzed and measured the density of the sampled testing gas with the industrial gas detectors or analyzers (38, 39, 40, and 41). If the density of the sampled testing gas is more than the predetermined value then few of the testing gas is discharged from the gas testing chamber from first chamber 50 and second chamber 51 via vacuum pump 49 and the injection of the zero air gas is controlled at steps 222-223.

If the density of the sampled testing gas is less than the predetermined value then the system 100 checks whether the density of the sampled testing gas is less than 20% at step 224. If the density of the sampled testing gas is less than 20% then the injection of diluted and mixed testing gases and the zero air gas are controlled at steps 219 and 220. If the density of the sampled testing gas is not less than 20% then the injection of pure testing gas and the zero air gas are controlled at steps 227 and 228.

At step 225, the performance of the gas leak detector test samples are controlled if the density of the sampled testing gas is equal to the predetermined value and as per the standard requirements according to, but not limited to, European standards No EN 50291-1 and EN 50194-1 and their equivalent American standards No UL 2034 and UL 1484. At step 226, the auditory alarms are controlled. At step 229, the system 100 made decisions for compliance or non-compliance of the gas leak detector test samples with standard requirements. At steps 230-231, the testing results are declared and the test first chamber 50 and second chamber 51 and the test gas pipelines 55 are cleaned after successful completion of the selected tests.

At step 232, the user/operator could check whether the selected tests are finished or not. If the selected tests are not finished then again, the user/operator could select the type of standard test and testing section at step 205. If the selected tests are successfully finished then a system administrator could confirm the test execution at step 233. At step 234, the test could renewal or re-execute if the system administrator could not confirm the test execution by the user/operator. If the system administrator is confirmed the test execution by the user/operator then the test execution process is successfully ended at step 235.

The advantages of the present invention include: the smart mechanized system 100 has potential for execution of all practical test sections in European standards No EN 50291-1 and EN 50194-1 within a perfect and continuous preheat process until declaring the test results. The mechanized system 100 also executes all the practical sections in American standards No UL 2034 and UL 1484 within a perfect and continuous preheat process until declaring the test results. The system 100 could execute the test for each section independently as part-by-part in sequentially and serially manner.

Also, the system 100 has the capability for monitoring and announcing of test results for each section independently. The system 100 displays and controls the different parameters of ambient conditions for testing execution. The different parameters include, but not limited to, temperature, moisture, air pressure, the operational voltage of the system 100, the velocity of testing gas, and sound intensity in testing execution ambiance using calibration equipment and precise tools as per the relevant standard requirements.

In addition, the system 100 displays and controls the compression and density of the testing gases within the first chamber 50 and the second chamber 51. The testing gases depend on using industrial gas detector or analyzers and could be, but not limited to, carbon monoxide (CO), methane ($CH_4$), nitrous oxide (NO), and sulfur dioxide ($SO_2$). The compression and concentration in testing gas are produced at least by two methods. The methods include sampling and analyzing of testing gas by the industrial gas detectors or analyzers and/or controlled gas injection using defined and reference gas. Further, the test execution and monitoring of all the operational processes are performed via online. The test execution includes, but not limited to, ambient conditions, preheat, production of testing gas with determined density, sampling status of testing gas, analysis on testing gas, circulation and homogenization of testing as in the test execution chambers, performance status of detectors, test results, hour and date of the test execution, and operator related parameters.

Further, the velocity of the tested gas is created by the circulation of the testing gases within the first chamber 50 and the second chamber 51. The first chamber 50 and the second chamber 51 consume and save more testing gases and eliminate the wastage of the testing gases after circulation and thus the cost of testing execution is lower than the conventional systems. Further, the system 100 includes a login module/system with a username and a password for any individuals and two security access levels, thereby accessing the facilities of the mechanized system and to eliminate the possible faults. The two security access levels are the first-degree access for system administrator and the second-degree access for operator or expert.

Further, the system 100 comprises the heating system 33, cooling system 34, humidifier 20 with cold or warm moisture generator, desiccator and dryer 56 for moisture. The system 100 has the potential to stop or renew/repeat the test process with respect to the access level of the individuals. Also, the system 100 could provide visual warning and alarm when the ambient conditions of test exit from the determined range. Further, the system 100 could stop the test execution process when ambient conditions of test exit from the determined range.

The system 100 cleans the gas transfer pipelines 55 and the test chambers or the first chamber 50 and the second chamber 51. The cleaning process is performed in two steps. Initially, the zero gas is supplied and then the ambient air is supplied to the gas transfer pipelines 55 and the first chamber 50 and the second chamber 51, where both gases (zero air and ambient air) are exhausted and discharged using the vacuum pump 49. Further, the system 100 generates the test results at least in three different formats such as printed, JPEG (Joint Photographic Experts Group) and PDF (Portable Document Format). The system 100 also verifies the operational process parameters such as temperature, moisture, gas pressure, the velocity of tested gas, sound intensity and the density of produced testing gas using calibration equipment and accurate tools which is in parallel with execution of standard tests synchronously.

The system 100 further comprises one or more gas purge system (7, 8, and 9). The gas purge systems (7, 8, and 9) are utilized to discharge the unclean, impure and intrusive gases from gas transfer pipelines and tubes. The system 100 further comprises an exclusive panel and one or more storage units. The exclusive panels are mounted for corrosive and non-corrosive gases with one or more regulators such as pressure reduction regulators and flow control regulators, and one or more valves such as electric valve and related one-way valves. The one or more storage units includes at least two separate and independent storage units. The storage units are utilized to keep consuming gas capsules and additional gas capsules based on the testing section and standards of running the tests.

The system 100 further comprises the uninterrupted power supply (UPS) 24 to supply power continuously to the system 100 during the electrical shutdown. The system 100 could provide highly precise performance with faster speed in the process of execution of tests. Further, the test results could be recorded and archived for future reference and use.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions.

Although specific terms may be employed herein, they are used only in generic and descriptive sense and not for purposes of limitation. Accordingly, the present invention is not limited to the specific embodiments illustrated herein. While the above is a complete description of the preferred embodiments of the invention, various alternatives, modifications, and equivalents may be used. Therefore, the above description and the examples should not be taken as limiting the scope of the invention, which is defined by the appended claims.

What is claimed is:

1. A testing mechanized system for testing one or more gas leak detectors by considering multiple operational parameters as per standard requirements, comprising:

one or more gas cylinders with purge systems configured to store testing gases with different concentrations;

a test execution chamber connected to the one or more gas cylinders via test gas pipelines and a plurality of valves, wherein the test execution chamber comprises a first chamber, a second chamber, measuring instruments and a data logger;

one or more mass flow controllers (MFCs) securely positioned between the one or more gas cylinders and the test execution chamber, wherein the mass flow controllers are configured to measure and control the flow of the testing gases; and one or more industrial gas leak detectors or analyzers securely connected to the second chamber of the test execution chamber via the test gas pipelines, sampling pumps, and a plurality of valves, thereby transferring the testing gases to the one or more industrial gas leak detectors or analyzers for verifying and testing the performance of one or more gas leak detectors test samples as per standard requirements;

wherein the multiple operational parameters include temperature, humidity, air pressure, velocity of testing gas, sound intensity, operational voltage of the gas leak detector, performance status of a cooling system, a heating system, a humidifier, a dryer, the sampling pumps, a vacuum pump, a circulation pump, a density of the testing gases with activation of a special industrial gas detector or analyzers of the same testing gas, a status of the plurality of valves, test results, hour and date of a test execution, operator related parameters, a performance status of the one or more gas leak detector test samples in terms of alarm and timetable for exiting from alarming status, indication and recording described timetables in standard requirements for activation of audiovisual alarms and exiting from alarming status, and potential for selection and injection of suitable testing gases for an operational test.

2. The system of claim 1, further comprises an uninterrupted power supply (UPS) for supplying power to the testing mechanized system and using an autotransformer and a digital voltmeter or volt transmitter thereby controlling operational voltage supplied to the one or more gas leak detectors and further wherein a humidifier is used to maintain or increase the humidity within the test execution chamber and a dryer is used to maintain or decrease the humidity within the test execution chamber.

3. The system of claim 1, further comprises a control system, wherein the control system is in communication with a monitoring system and the testing mechanized system, thereby enhancing control of the operation of the testing mechanized system for testing one or more gas leak detector test samples by considering operational parameters, wherein the one or more gas leak detectors are carbon monoxide and flammable gases leakage detectors.

4. The system of claim 3, wherein the control system includes a programmable logic controller (PLC) and/or a microprocessor and/or microcontroller for controlling the operation of the testing mechanized system.

5. The system of claim 1, wherein the in the first chamber and the second chamber of the test execution chamber are connected to form a closed cycle, thereby providing the potential for saving in consumption of the testing gases, wherein velocity of testing gases between first chamber and second chamber is made with a circulation pump and controlled via a dimmer.

6. The system of claim 1, wherein the testing gases are at least any one or any combination of a zero air gas, pure gases ($CO/CH_4$), diluted gases ($CO/CH_4$), mixed gases ($H_2$, $CO$, $CO_2$), a hexamethyldisiloxane gas, an ethanol gas, a toluene gas, an acetone gas, a nitric oxide (NO) gas, and a sulfur dioxide ($SO_2$) gas.

7. The system of claim 1, wherein the test execution chamber further comprises one or more sensors and transmitters and devices for monitoring and controlling the test execution chamber, wherein the one or more sensors and transmitters and devices are at least any one or any combination of a temperature sensor, a humidity sensor, an air pressure sensor, an audiometer, a digital air anemometer, and the data logger.

8. The system of claim 1, wherein the test execution chamber further comprises a heating system and a cooling system, wherein the heating system and the cooling system are configured to adjust the temperature, thereby maintaining stability in the test execution chamber for controlling under conditions of ambient temperature.

9. A method for testing one or more gas leak detector test samples using a testing mechanized system by considering multiple operational parameters as per standard requirements, comprising the steps of:

Vacuuming existing air from a test execution chamber, wherein the test execution chamber comprises first and second execution chambers, calculating injection time due to first and second execution chambers' volume capacity, testing gas concentration, and testing gases flow ratio due to mass flow controllers (MFCs), afterward, transferring, controlled injecting and uniformly circulating one or more testing gases with different and defined concentrations from one or more gas cylinders into a test execution chamber via test gas pipelines, a plurality of valves, and one or more mass flow controllers (MFCs);

performing a sampling process by obtaining a part of the testing gas within the test execution chamber via a sampling pump and sampling probe and then analyzing the sampled testing gas with industrial gas detectors or analyzers;

controlling the performance of the one or more gas leak detector test samples as per standard requirements by adjusting the density of the referenced or sampled testing gas to a predetermined value and as per the standard requirements;

making decision for compliance or non-compliance of the one or more gas leak detector test samples with the standard requirements, and declaring testing results of the one or more gas leak detector test samples and, thereby verifying and testing the performance of the one or more gas leak detector test samples as per the standard requirements.

10. The method of claim 9, wherein the testing mechanized system comprises an uninterrupted power supply (UPS) for supplying power to the testing mechanized system and using an autotransformer and a digital voltmeter or volt transmitter, thereby controlling the operational voltage supplied to the one or more gas leak detectors and further wherein a humidifier is used to maintain or increase the humidity within the test execution chamber and a dryer is used to maintain or decrease the humidity within the test execution chamber.

11. The method of claim 9, wherein the testing mechanized system further comprises a control system, wherein the control system is in communication with a monitoring system and the testing mechanized system, thereby controlling the operation of the testing mechanized system for testing the one or more gas leak detector test samples by considering multiple operational parameters and different concentration of pure or/and diluted or/and mixed testing gases.

12. The method of claim 11, wherein the control system includes a programmable logic controller (PLC) and/or a microprocessor and/or microcontroller for controlling the operation of the testing mechanized system.

13. The method of claim 9, wherein the first chamber and the second chamber of the test execution chamber are connected to form a closed cycle, thereby providing the potential for saving in consumption of the testing gases, wherein velocity of testing gases between first chamber and second chamber is made with a circulation pump and controlled via a dimmer.

14. The method of claim 9, wherein the testing gases are at least any one or any combination of a zero air gas, pure gases ($CO/CH_4$), diluted gases ($CO/CH_4$), mixed gases ($H_2$, CO, $CO_2$), a hexamethyldisiloxane gas, an ethanol gas, a toluene gas, an acetone gas, a nitric oxide (NO) gas, and a sulfur dioxide ($SO_2$) gas.

15. The method of claim 9, wherein the test execution chamber further comprises one or more sensors and transmitters and devices for monitoring and controlling the test execution chamber, wherein the one or more sensors and transmitters and devices are at least any one or any combination of a temperature sensor, a humidity sensor, an air pressure sensor, an audiometer, a digital air anemometer, and a data logger.

16. The method of claim 9, wherein the test execution chamber further comprises a heating system and a cooling system, wherein the heating system and the cooling system are configured to adjust the temperature, thereby maintaining stability in the test execution chamber for controlling under conditions of ambient temperature.

17. The method of claim 9, wherein the multiple operational parameters include temperature, humidity, air pressure, velocity of testing gas, sound intensity, operational voltage of the gas leak detector, performance status of a cooling system, a heating system, a humidifier, a dryer, the sampling pumps, a vacuum pump, a circulation pump, a density of the testing gases with activation of a special industrial gas detector or analyzers of the same testing gas, a status of the plurality of valves, test results, hour and date of a test execution, operator related parameters, a performance status of the one or more gas leak detector test samples in terms of alarm and timetable for exiting from alarming status, indication and recording described timetables in standard requirements for activation of audiovisual alarms and exiting from alarming status, and potential for selection and injection of suitable testing gases for an operational test.

18. The method of claim 9, wherein the density and concentration of the made testing gas is adjusted as per the standard requirements by controlling the timeable injections or sampling result of the zero air and/or pure and/or diluted and/or mixed testing gases are at least any one or any combination of a zero air gas, pure gases ($CO/CH_4$), diluted gases ($CO/CH_4$), mixed gases ($H_2$, CO, $CO_2$), a hexamethyldisiloxane gas, an ethanol gas, a toluene gas, an acetone gas, a nitric oxide (NO) gas, and a sulfur dioxide ($SO_2$) gas within the test execution chamber.

* * * * *